United States Patent
Kunz

(10) Patent No.: US 7,704,494 B2
(45) Date of Patent: Apr. 27, 2010

(54) METHOD FOR PRODUCING PLANT PROTECTION OR PLANT-STRENGTHENING AGENT FOR FIGHTING AGAINST BACTERIAL AND/OR FUNGAL PLANT DISEASES, IN PARTICULAR AGAINST FIRE BLIGHT

(75) Inventor: Stefan Kunz, Radolfzell (DE)

(73) Assignee: Bio-Protect GmbH, Constance (DE)

( * ) Notice: Subject to any disclaimer, the term of this patent is extended or adjusted under 35 U.S.C. 154(b) by 224 days.

(21) Appl. No.: 10/575,434

(22) PCT Filed: Sep. 14, 2004

(86) PCT No.: PCT/EP2004/010258

§ 371 (c)(1),
(2), (4) Date: Apr. 10, 2006

(87) PCT Pub. No.: WO2005/048717

PCT Pub. Date: Jun. 2, 2005

(65) Prior Publication Data

US 2007/0141031 A1     Jun. 21, 2007

(30) Foreign Application Priority Data

Oct. 21, 2003   (DE) .............................. 103 49 413.8

(51) Int. Cl.
*A01N 63/04* (2006.01)
*A01N 25/00* (2006.01)
*A01N 63/00* (2006.01)

(52) U.S. Cl. ................ 424/93.5; 424/93.51; 504/116.1; 504/117; 504/118

(58) Field of Classification Search ..... 424/93.5–93.51; 504/117–149
See application file for complete search history.

(56) References Cited

U.S. PATENT DOCUMENTS

2002/0166147 A1 * 11/2002 Jabar et al. .................. 800/298

FOREIGN PATENT DOCUMENTS

JP         06256125 A  *  9/1994

OTHER PUBLICATIONS

Seibold et al., Hefen als Antagonisten gegen Feuerbrand [online], Abstract of presentation given at Arbeitskreis Phytobakteriologie Conference, Sep. 11-12, 2003 [Retrieved Oct. 2, 2007], Retrieved from Internet: <http://www.phytomedizin.org/fileadmin/alte_Webseiten/ak/11/tagung2003.htm>.*
JP 06256125 A (Eizai Seika Ken Kk [Eizian]) 1994-329870 (abstract) World Patents Index [online]. London, U.K.: Derwent Publications, Ltd. [Retrieved on Oct. 2, 2007].*

* cited by examiner

*Primary Examiner*—Ruth A. Davis
*Assistant Examiner*—Sheridan R Macauley
(74) *Attorney, Agent, or Firm*—Bachman & LaPointe, P.C.

(57) ABSTRACT

A method for producing plant protection or plant-strengthening agent for fighting against bacterial and/or fungal plant diseases, in particular against a fire blight consisting in adding capable to proliferate fungal structures into an acid medium for treating plants.

8 Claims, No Drawings

METHOD FOR PRODUCING PLANT PROTECTION OR PLANT-STRENGTHENING AGENT FOR FIGHTING AGAINST BACTERIAL AND/OR FUNGAL PLANT DISEASES, IN PARTICULAR AGAINST FIRE BLIGHT

BACKGROUND OF THE INVENTION

Such methods for producing plant protection or plant-strengthening agent for controlling bacterial and/or fungal plant diseases, in particular for controlling fire blight, are known in a variety of forms and embodiments.

It is known that antagonistic microorganisms are employed more and more often. Besides bacteria such as, for example, *Bacillus thuringiensis*, which are used as insecticides, or *Bacillus subtilis*, which are used in soil treatment agents and seed-dressing products, there are also preparations comprising fungal spores and yeast cells.

A known example is the plant protection production Contans, which comprises spores of *Coniothyrium minitans,* or various preparations with the yeast *Trichoderma harzianum.* These preparations are essentially applied to the soil or incorporated into the soil or garden compost. These agents are not suitable for floral application.

The disadvantage is that fire blight of pome fruit is caused by the bacterium *Erwina amylovora*. It is controlled for example by plant management methods and sanitation, for example by grubbing up the plants, for example reduction of the inoculum. Fire blight is furthermore controlled by means of plant protection agents. Frequently, treatments with antibiotics are carried out during flowering. Here, the active substance streptomycin, whose activity is well known, is used. However, this plant protection agent has recently been banned, or will be banned all over the EU. The active substance streptomycin, which the plant protection agent plantomycin contains, has been used successfully in the United States since the 70s; however, problems with resistant pathogens are on the increase, which is undesired.

Also known are treatments with copper during flowering, for example with funguran, cuprozin; however, they must not be carried out in the case of dessert fruit as the result of phytotoxic effects. Moreover, the license of this agent has already expired in December 2002.

Moreover, there have been attempts to apply antagonistic microorganisms to the flowers of fruit trees and thus to inhibit the growth of pathogen and thus to prevent infection. Various bacteria such as *Pseudomonas flourescens, Pantoea agglomerans, Bacillus subtilis, Rhanella aquatilis*, have been employed in this context. In some cases, saleable products were developed with these bacteria, such as, for example, the products Blight ban and Serenade in the USA and BIOPRO in Germany. The effects of these products are very dubious to date, and their use is very limited.

It is therefore an object of the present invention to provide a method for producing plant protection agent for controlling bacterial and/or fungal plant diseases, in particular fire blight, and a plant protection agent and its use which overcome the above-mentioned disadvantages and which can be employed highly effectively for a multiplicity of plants, in particular fruit plants. In this context, it is intended that the plant protection agent can be applied to the diseased plants in sprayable form.

SUMMARY OF THE INVENTION

The object is achieved by providing a method for producing plant protection or plant-strengthening agents for controlling bacterial and/or fungal plant diseases, in particular fire blight, characterized in that fungal structures which are capable of multiplication are added to an acidic environment for the treatment of plants.

The method is characterized in that the acidic environment is kept within a pH range of from 3 to 6, preferably pH 3.6 to 4.0.

The method is characterized in that the fungal structures added are yeast cells and/or fungal spores which are capable of multiplication.

The method is characterized in that blastospores of the species *Aureobasisium pullulans* are added.

The method is characterized in that yeast cells of the species *Metschnikowia pulcherrima* are added.

The method is characterized in that citric acid is added as acidifier.

The method is characterized in that whey powder is added to the environment.

The method is characterized in that blastospores or yeast cells and citric acid and whey powder are added.

The method is characterized in that disodium hydrogen phosphate or sodium hydrogen carbonate is added to the environment.

The method is characterized in that spores, conidia and budding yeast cells of filamentous fungi and yeast are used as fungal structures which are capable of multiplication.

The method is characterized in that fire blight (*Erwinia amylovora*) is controlled by spraying flowers of plants with a mixture of fungal structures which are capable of multiplication and acids whose spray mixture is in a pH range of approximately from 3 to 6.

The method is characterized in that fire blight (*Erwinia amylovora*) is controlled by spraying flowers of plants with blastospores of the species Aureobasisium pullulans and/or yeast cells of the species Metschnikowia pulcherrima in a mixture with acid, the mixture or spray mixture being maintained within a pH range of from 3 to 6.

The method is characterized in that for the control of fire blight (*Erwinia amylovora*) flowers of plants are sprayed with blastospores of the species *Aureobasisium pullulans* and/or yeast cells of the species *Metschnikowia pulcherrima* in a mixture with organic acids whose pH is in the range of approximately from 3 to 6.

A plant protection or plant-strengthening agent for controlling bacterial and/or fungal plant diseases, in particular fire blight, characterized in that the product comprises an acidic environment and fungal structures which are capable of multiplication. A plant protection or plant-strengthening agent for controlling bacterial and/or fungal plant diseases, in particular fire blight, characterized in that 1 kg of product comprises:

approx. $2\times10^{11}$ to $1\times10^{13}$, in particular $2\times10^{12}$ blastospores of the species *Aureobasisium pullulans* approx. $2\times10^{11}$ to $1\times10^{13}$, in particular $3\times10^{12}$ yeast cells of the species *Metschnikowia pulcherrima*

100 g to 400 g, in particular 300 g of citric acid 50 g to 250 g, in particular 150 g of disodium hydrogen phosphate 100 g to 500 g, in particular 400 g of whey powder.

The use is characterized plant protection or plant-strengthening agent for controlling bacterial and/or fungal plant diseases, in particular fire blight, comprise, in an acidic environment, fungal structures which are capable of multiplication.

The use is characterized in that blastospores of the species *Aureobasisium pullulans* and/or yeast cells of the species *Metschnikowia pulcherrima* are used as fungal structures which are capable of multiplication.

The use is characterized in that organic or inorganic acidifiers, in particular citric acid, are used.

The use is characterized in that the environment used is an acidic environment within a pH range of from 3 to 6, in particular from 3.6 to 4.0.

The use is for a 1-kg product of plant protection or plant-strengthening agent:
- approx. $2 \times 10^{11}$ to $1 \times 10^{13}$ in particular $2 \times 10^{12}$ blastospores of the species *Aureobasisium pullulans*
- approx. $2 \times 10^{11}$ to $1 \times 10^{13}$, in particular $3 \times 10^{12}$ yeast cells of the species Metschnikowia pulcherrima
- 100 g to 400 g, in particular 300 g of citric acid
- 50 g to 250 g, in particular 150 g of disodium hydrogen phosphate
- 100 g to 500 g, in particular 400 g of whey powder.

The use is characterized in that spores, conidia and budding yeast cells of filamentous fungi and yeasts are used as fungal structures.

The use is characterized in that the product is used as spray mixture within a pH range of from 3 to 6 for spraying diseased flowers of plants.

DETAILED DESCRIPTION

The present invention creates a plant protection product or plant-strengthening agent in which fungal structures which are capable of multiplication, preferably yeast cells and/or fungal spores, are introduced or added into an acidic application within a pH range of from 3 to 6, preferably from 3.6 to 4.0.

A product which is resuspended in water for the treatment of plants consists of whey powder, disodium hydrogen phosphate, citric acid and blastospores of strain CF10 of the species *Aureobasidium pullulans* and yeast cells of strain MSK1 of the species *Metschnikowia pulcherrima*. This product is particularly suitable for the control of fire blight.

The efficacy of the novel plant protection or plant-strengthening agent has even outperformed the antibiotic plantomycin.

In this context, it is possible to use fungal structures which are capable of multiplication, such as spores, conidia and budding yeast cells of filamentous fungi and yeasts which are preferably added to the spray mixture within a pH range of from 3 to 6. In connection with the present invention, it has been shown as particularly advantageous that the use of fungal spores or yeast cells in admixture with organic or inorganic acid results in a specific increase in activity in the control of fire blight. In particular, adding the fungal spores or yeast spores to an acidic environment which can be sprayed, or spray mixture, results in an increased efficacy in the control of bacterial and/or fungal plant diseases. The pathogens causing fire blight can be controlled very efficiently and with very low outlay in this manner.

I claim:

1. A method for controlling fire blight, comprising providing an acidic environment comprising (1) fungal structures selected from the group consisting of yeast cells, fungal spores and mixtures thereof, and (2) at least one of disodium hydrogen phosphate and sodium hydrogen carbonate in an amount sufficient to maintain a pH of the acidic environment between 3.4 to 4.0; and applying the acidic environment to a plant.

2. The method as claimed in claim 1, wherein the fungal structures comprise blastospores of the species *Aureobasidium pullulans*.

3. The method as claimed in claim 1, wherein the fungal structures comprise yeast cells of the species *Metschnikowia pulcherrima*.

4. The method as claimed in claim 1, including adding citric acid as acidifier.

5. The method as claimed in claim 1, including adding whey powder.

6. The method as claimed in claim 1, wherein providing an acidic environment comprises adding (1) blastospores or yeast cells, (2) citric acid and (3) whey powder.

7. The method as claimed in claim 1, wherein the fungal structures comprise spores, conidia and budding yeast cells of filamentous fungi and yeast , and wherein the fungal structures are capable of multiplication.

8. A plant protection agent for controlling fire blight, wherein 1 kg of product comprises:
- $2 \times 10^{11}$ to $1 \times 10^{12}$ blastospores of the species *Aureobasidium pullulans;*
- $2 \times 10^{11}$ to $1 \times 10^{13}$ yeast cells of the species *Metschnikowia pulcherrima;*
- 100 g to 400 g citric acid;
- 50 g to 250 g disodium hydrogen phosphate; and
- 100 g to 500 g whey powder.

\* \* \* \* \*